United States Patent [19]

Sharp et al.

[11] 4,335,756
[45] Jun. 22, 1982

[54] STERILIZED MEDICAL TUBING COVER

[75] Inventors: Russell G. Sharp, Sugar Land; Charles C. Reed, Houston; Denton A. Cooley, Houston; Terry N. Crane, Houston; William R. Wilkinson, Missouri City, all of Tex.

[73] Assignee: Texas Medical Products, Inc., Houston, Tex.

[21] Appl. No.: 226,657

[22] Filed: Jan. 21, 1981

[51] Int. Cl.³ .............. F61L 55/10; A61M 1/00; A61B 19/02; A61M 25/00
[52] U.S. Cl. .............. 138/89; 138/96 R; 206/363; 206/364; 220/352; 220/356
[58] Field of Search .............. 206/363, 364, 306, 438, 206/210, 205, 303; 138/96 R, 96 T, 89; 220/352, 356

[56] References Cited

U.S. PATENT DOCUMENTS

| 3,283,894 | 11/1966 | Hafner et al. | 206/306 |
| 3,350,044 | 10/1967 | Zulauf | 138/96 R |
| 3,918,920 | 11/1975 | Barber | 206/306 |
| 3,934,721 | 1/1976 | Juster et al. | 206/364 |
| 3,948,290 | 4/1976 | Arisland | 138/96 R |
| 3,987,930 | 10/1976 | Fuson | 138/96 R |
| 4,139,023 | 2/1979 | Turley | 138/96 T |

Primary Examiner—William T. Dixson, Jr.
Attorney, Agent, or Firm—H. Ross Workman; Allen R. Jensen; Rick D. Nydegger

[57] ABSTRACT

The present invention is directed to an improved cover for enclosing the ends of medical tubing and which is capable of maintaining the sterile condition of the tubing prior to its use in surgical or medical procedures. The cover is designed with an inner diameter of constant cross section and with several tapered ribs along the surface of the inner wall of the cover.

7 Claims, 6 Drawing Figures

STERILIZED MEDICAL TUBING COVER

BACKGROUND

1. The Field of Invention

The present invention is directed to a cover for medical tubing. More particularly, the present invention relates to a medical tubing cover which encloses the ends of sterilized medical tubing and which can be easily removed from the tubing prior to use in surgical or other medical procedures.

2. The Prior Art

In recent years it has become increasingly popular to utilize pre-cut medical tubing packaged and sterilized within an airtight container. The container may be opened in the sterile field of the operating room and the medical tubing can be directly coupled into a fluid circuit without the need of measuring, cutting, or sterilizing the tubing. Thus, it will be appreciated that the availability of pre-cut, pre-sterilized medical tubing in a variety of lengths and diameters greatly simplifies the "scrub procedure" involved in constructing a fluid circuit.

It is well known in the art that it is desirable to enclose the ends of medical tubing after it has been sterilized so that the sterile condition may be maintained. Furthermore, in the case of the packaged medical tubing described above, it is desirable to provide covers at the ends of the medical tubing which (1) allow the sterilizing agent to pass through the tubing while it is within the airtight container, and which (2) preserve the aseptic condition of the medical tubing once the container is opened. Such covers, commonly referred to as "breather caps", are found in the prior art as described hereinafter.

The covers found in the prior art are typically injection molded having one closed end and the other end open so as to receive the end of the medical tubing in mating relationship. The walls of the prior art covers are tapered having a gradually reduced diameter so that, as the cover is advanced onto the tubing, the walls of the cover are stretched by the advancing tubing within the cover. This stretching action causes the outer surfaces of the tubing to come into contact with the inner wall surface of the cover, thereby "sealing" the end of the tubing.

In order to permit a sterilizing agent to pass through the tubing, it has been necessary to punch a hole in the closed end of the cover. However, this design is potentially dangerous. For example, it is not uncommon for the punched-out portion of the cover to remain loosely connected to the interior wall of the cover and then fall into the medical tubing between the time the tubing is packaged and used. Thus, it will be appreciated that the insoluble, punched-out portion of the cover could cause extreme complications if inadvertantly introduced into an extracaporeal fluid circuit.

Another disadvantage is that it is often difficult to remove the cover from the tubing prior to its use. This difficulty in removal is caused by the retention forces of the cover. Because the cover is stretched over the tubing, the retention forces are related to the elasticity of the material from which the cover is made. Furthermore, as the surface area of contact between the inner wall of the cover and the outer surface of the tubing increases, there is a substantial increase in the frictional forces. The prior art covers are even more difficult to remove because they are typically made from a "tacky" plastic material which has relatively high coefficient of friction.

To overcome these problems to a limited extent, covers are found in the prior art which utilize tapered walls and a plurality of spaced-apart ribs of uniform cross-sectional height located on the inner wall surfaces of the cover. Such a prior art cover is illustrated in FIGS. 1 and 2 of the drawing. It will be noted that since the ribs are relatively narrow, the surface area of contact between the inner wall of the cover and outer surface of the tubing is reduced, thereby minimizing the frictional forces.

However, while the use of such ribs provides some improvement over the previous designs, it will be appreciated that there still exists considerable retention forces since the wall of the cover must be stretched in order for the cover to be held in place. In fact, the prior art covers illustrated in FIGS. 1 and 2 have even higher retention forces because of the effective increase in the thickness of the wall, caused by the ribs. Great difficulty has therefore, been experienced in removing such covers. Since the purpose of these covers is to act as a sterile barrier, it is very important that they be secure without being too difficult to remove. When the covers are difficult to remove, technique errors, which compromise the sterility of the tubing, can occur.

BRIEF DESCRIPTION AND OBJECTS OF THE INVENTION

The present invention is directed to a new and improved medical tubing cover which permits the passage of a sterilizing agent therethrough for sterilizing medical tubing, and which is thereafter capable of maintaining the sterile condition of the tubing prior to its use in medical or surgical procedures. The present invention is further directed to a new and improved medical tubing cover which is capable of being easily removed from the medical tubing. The cover of the present invention is preferably made from a "dry" plastic material having a relatively small coefficient of friction. The cover is designed such that the wall forms an internal diameter of uniform cross section and such that the ribs along the inner wall surfaces increasingly taper toward the rear of the cover, thereby providing an effectively decreasing internal diameter within the cover. The cover is also preferably provided with a knob which aids in removing the cap from the sterilized medical tubing.

It is, therefore, a primary object of the present invention to provide covers for the ends of sterilized medical tubing which are capable of maintaining the sterile condition of the tubing until the time of use in medical and surgical procedures.

It is another object of the present invention to provide a cover for the ends of medical tubing which permit the passage of a sterilizing agent therethrough.

It is an even further object of the present invention to provide a medical tubing cover which is easily removable from the sterilized medical tubing without compromising the sterile condition of the tubing.

These objects and features of the present invention will become more fully apparent from the following description and appended claims taken in conjunction with the accompanying drawings.

DESCRIPTION OF THE PREFERRED EMBODIMENT

Reference is now made to the drawings wherein like parts are designated with like numerals throughout.

Figure 1:
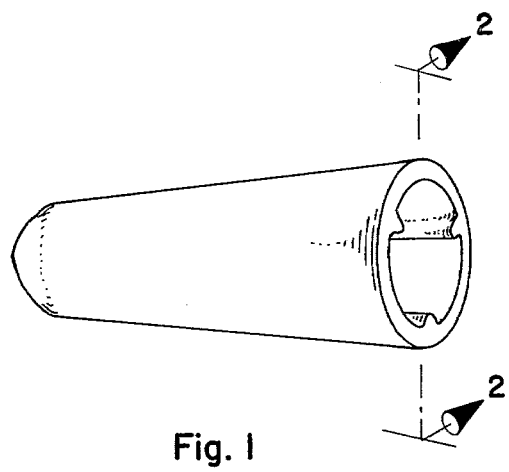
FIG. 1 is a perspective view of a medical tubing cover of the prior art.
Figure 2:
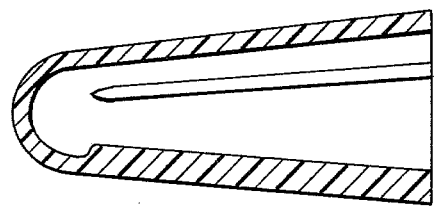
FIG. 2 is a cross-sectional view of the medical tubing cover of FIG. 1 of the prior art taken along line 2—2 of that figure.
Figure 3:
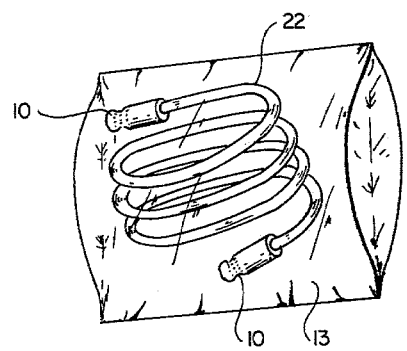
FIG. 3 is a perspective view of a length of medical tubing having tubing covers of the present invention thereon, which tubing is enclosed in an air tight container.

As discussed previously, the cover illustrated in FIGS. 1 and 2 is well known in the prior art. A medical tubing cover within the scope of the present invention is illustrated in FIGS. 3–6. FIG. 3 shows cover 10 and tubing 22 enclosed in airtight package 13 such that the covers engage the ends of a length of medical tubing. Also present within package 13 during the sterilization process is a sterilizing agent, e.g., ethylene oxide gas, which is capable of sterilizing tubing 22.

Figure 4:
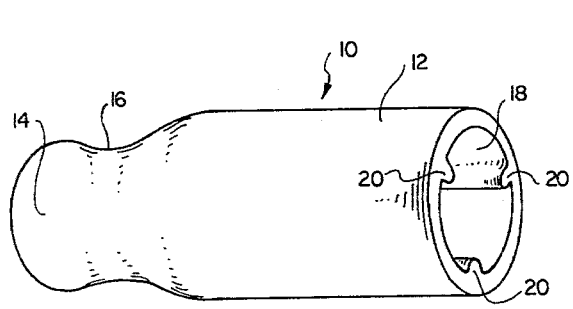
FIG. 4 is a perspective view of a medical tubing cover within the scope of the present invention.

With particular reference to FIG. 4, cover 10 has a wall portion 12 and a gripping portion 14. Gripping portion 14 can be easily formed by creating an area of reduced diameter in wall portion 12 such as is generally designated by 16, at a point beyond where the medical tubing will be inserted within the cover.

Cover 10 may be made of a variety of materials; however, it is preferable that it be made of plastisol vinyl chloride. This material is a "dry" plastic which has a low coefficient of friction. Such a material is preferable since the frictional forces between the areas of contact of the cover and the tubing is reduced as compared to prior art covers which are typically made of polyvinyl chloride. Wall portion 12 forms a cylindrical opening into which tubing 22 is inserted; this opening has a uniform internal diameter along that portion of its length into which the tubing is inserted.

Several ribs 20 are formed on the inner surface of wall 12; each rib extends longitudinally from opening 18 towards diameterally reduced area 16. While any number of ribs may be utilized, the use of at least three ribs provides a sufficient number of points around the inner wall surface of the cover to preclude substantial areas of surface contact between tubing and the inner surface of wall 12. However, if too many ribs are utilized, the frictional forces caused by contact between the ribs and the outer surface of the tubing are greatly increased, thereby defeating the very purpose of using the ribs to achieve easy removal of the cover from the tubing. Accordingly, three or four ribs spaced at equal distant intervals about the inner wall surface of the cover are presently preferred.

Figure 5:
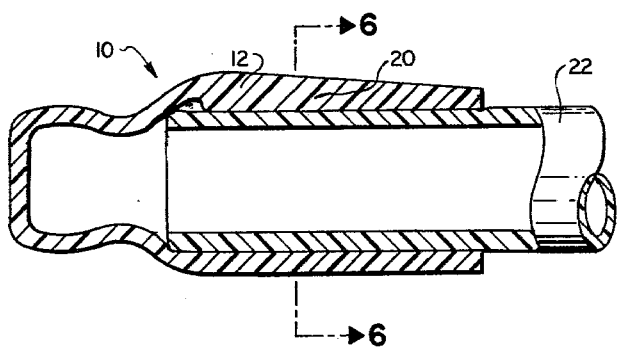
FIG. 5 is a cross-sectional view of an embodiment of the medical tubing cover of the present invention which has been placed over the end of a length of medical tubing.

As illustrated in FIG. 5, the cross-sectional height of rib 20 increases with the distance from opening 18. (It will be appreciated that the increase in the height of rib 20 has been exaggerated in the drawings for purposes of illustration.) Since the diameter formed by the inner surface of wall 12 is constant, the plurality of ribs effectively reduces the diameter within the rear portion of the cover, i.e., as the distance increases from opening 18.

Figure 6:
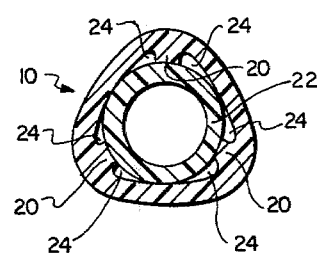
FIG. 6 is a cross-sectional view taken along lines 6—6 of FIG. 5.

When tubing 22 is inserted into cover 10, as illustrated in FIG. 5, the tubing 22 first contacts ribs 20. As tubing 22 is pushed further into cover 10, ribs 20 are forced outwardly, away from tubing 22. However, unlike prior art covers, as the cover is advanced onto the end of tubing 22, wall 12 of the cover of the present invention is deformed. That is to say, the wall portion between ribs 20 loses its rounded configuration and becomes somewhat flattened, as depicted in FIG. 6. In an exaggerated sense, when three ribs are used, an end view of the wall 12 of cap 10 would begin to take a triangular shape rather than a circular shape. Therefore, as distinguished from prior art covers, the walls of the covers of the present application are deformed in shape rather than being stretched.

The retention forces of a cover of the present invention comes from the tendency of the plastic material of the cover to return to its natural cylindrical shape. Such retention forces are sufficient to hold the cover on the end of tubing 22, but are not as great as the retention forces created in prior art devices where the force is dependent upon the elasticity of the material forming the cover.

Furthermore, frictional forces are minimized in the present design because the surface area of the inner wall contacting the tubing is kept to a minimum. Because the ribs are of increased height toward the rear of cap 10, the further that tubing 22 is inserted into cover 10, the greater the distance between the inner surface of wall 12 of the cover and tubing 22. Therefore, unlike the prior art devices where large areas of the wall portion are in direct contact with the outer surface of the tubing, only a minimal portion of wall 12 of the cover is in contact with tubing 22. Moreover, the portions of the inner wall surfaces adjacent to ribs 20 are spaced from tubing 22, thereby forming a plurality of channels 24. When placed in an atmosphere of etheylene oxide gas, such as in airtight package 13, the gas may pass through channels 24 and into tubing 22 to sterilize the interior of tubing 22.

The most common diameters of tubing used in medical and surgical procedures are $\frac{1}{4}$ inch, $\frac{3}{8}$ inch, $\frac{1}{2}$ inch, and $\frac{5}{8}$ inch. The diameters of the covers are, appropriately sized to fit these popular sizes of tubing. The thickness of wall 12 is typically about 1/16 to 3/32 of an inch. It has been found preferable that for the above-identified sizes of tubing, the taper on ribs 20 should be about 0.05 inch per inch of the cover. Although it may be preferable to use different rib sizes and tapers for each size of tubing cover, it has been found acceptable to use exactly the same size and taper of rib for all sizes of tubing covers. Since about one inch of the tubing is typically inserted into the cover, the effective inner diameter (the diameter defined by the ribs for a given cross section) of the cover decreases by about 0.1 inch over the length of the cover. For the $\frac{5}{8}$ inch diameter tubing cover, this taper represents a decrease in the effective inner diameter of approximately 15% of the tubing diameter over the length of the cover. For the $\frac{1}{4}$ inch diameter tubing cover the decrease in effective inner diameter is on the order of 40%. This has been found to be sufficient to accomplish the features set out hereinbefore.

Gripping portion 14 provides the user with a better gripping surface which is useful in removing the cap 10 from tubing 22. It will be appreciated that such a knob may be formed in one of any of a variety of ways so long as to provide a means for the doctor, nurse, or technician to easily get hold of the cover in order to remove it from the end of the tubing.

The present invention may be embodied in other specific forms without parting from the spirit or essential characteristics. The described embodiments are to be considered in all respects only as illustrative and not restrictive. The scope of the invention is, therefore, indicated by the appendent claims rather than the foregoing description. All changes which come within the meaning and range of equivalency of the claims are to be embraced within this scope.

What is claimed and desired to be secured by United States Letters Patent is:

1. A cover for tubing comprising:
   a tubular portion having first and second ends and having an inner surface which forms an opening of generally uniform diameter, said first end being configured to receive the tubing within the opening, said tubular portion being formed from a flexible material; and
   a plurality of rib members formed on the inner surface of the tubular portion, said rib members being of increasing cross-sectional height from the first end to the second end of said tubular portion, such that said rib members form a diameter within the opening which is smaller than the outer diameter of the tubing, whereby the walls of said tubular portion between said plurality of rib members are deformed from cylindrical shape when the end of a length of tubing is inserted therein.

2. A cover as defined in claim 1 further comprising gripping means for use in removing the cover, said gripping means being formed at the second end of the tubular portion.

3. A cover as defined in claim 1 wherein said rib members are evenly spaced about the inner surface of the tubular portion.

4. A cover for preserving the sterile condition of tubing to be used in medical procedures comprising:
   a tubular portion formed from a flexible material and having an inner diameter of generally uniform cross-section, which diameter is larger than an outer diameter of the tubing, said tubular portion having a first end forming an opening such that the tubing can be inserted therein;
   a second end of the tubular portion being closed so as to maintain the sterile condition of the tubing;
   at least three rib members integrally formed on an inner surface of the tubular portion, each of said rib members having an increased cross-sectional height from the first end to the second end of the tubular portion such that the diameter formed by the rib members decreased from the first end to the second end, whereby the walls of said tubular portion between said plurality of rib members are deformed from cylindrical shape when the end of a length of tubing is inserted therein.

5. A cover as defined in claim 4 wherein said second end of the tubular portion is provided with a gripping means for removal of said cover from the tubing which is inserted therein.

6. A cover as defined in claim 4 comprising three rib members equidistantly spaced about the inner surface of the tubular portion.

7. A cover as defined in claim 4 wherein the diameter formed by the rib members decreases from the first end to the second end by an amount from about 15% to about 40% of the diameter of said tubular portion.

* * * * *

UNITED STATES PATENT AND TRADEMARK OFFICE
CERTIFICATE OF CORRECTION

PATENT NO. : 4,335,756
DATED : June 22, 1982
INVENTOR(S) : Russell G. Sharp et al.

It is certified that error appears in the above—identified patent and that said Letters Patent are hereby corrected as shown below:

In Claim 4, (column 6, line 21) "decreased" should be
--decreases--

Signed and Sealed this

Twenty-fourth Day of August 1982

[SEAL]

Attest:

GERALD J. MOSSINGHOFF

Attesting Officer    Commissioner of Patents and Trademarks